United States Patent [19]

Sasaki et al.

[11] 4,258,030

[45] Mar. 24, 1981

[54] UROKINASE PREPARATION FOR ORAL ADMINISTRATION

[75] Inventors: Koji Sasaki, Omiya; Yasukazu Harada, Tokyo, both of Japan

[73] Assignee: Zeria-Shinyaku Kogyo Kabushiki Kaisha, Tokyo, Japan

[21] Appl. No.: 18,240

[22] Filed: Mar. 7, 1979

[51] Int. Cl.$^3$ ............... A01N 63/02; A61K 37/00; C07C 103/52; C12N 9/99
[52] U.S. Cl. .............................. 424/94; 424/177; 260/112.5 R; 435/188; 435/184; 435/215
[58] Field of Search ....................... 424/94, 177; 260/112.5 R; 435/184, 188, 215

[56] References Cited

U.S. PATENT DOCUMENTS

| | | | |
|---|---|---|---|
| 3,726,969 | 4/1973 | Johnson et al. | 424/94 |
| 3,919,414 | 11/1975 | Herrin et al. | 424/94 |

*Primary Examiner*—Delbert R. Phillips
*Attorney, Agent, or Firm*—Scrivener, Clarke, Scrivener and Johnson

[57] ABSTRACT

Disclosed is a urokinase preparation for oral administration which is effective for remedy of thrombosis such as cerebral thrombosis and cardiac infarction. This preparation comprises urokinase and, incorporated therein, an enzyme inhibitor.

11 Claims, 5 Drawing Figures

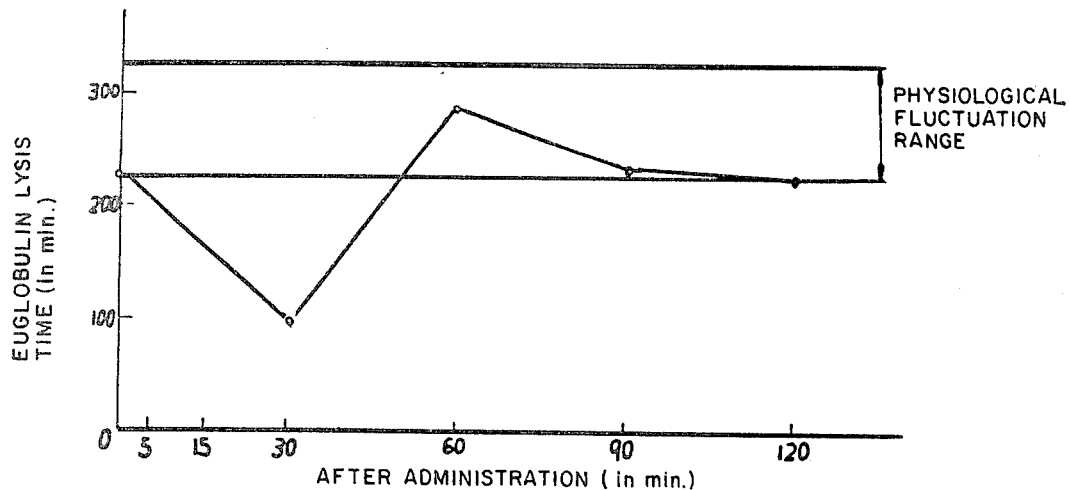
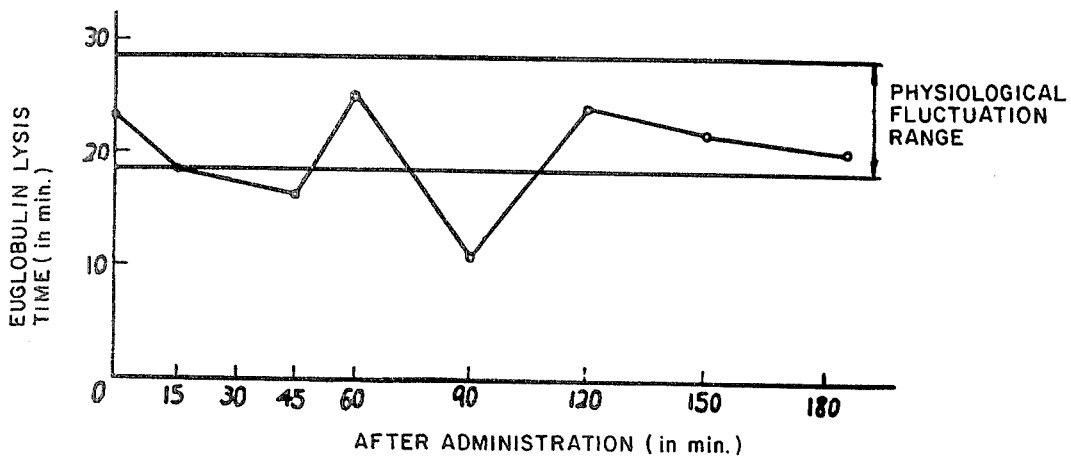
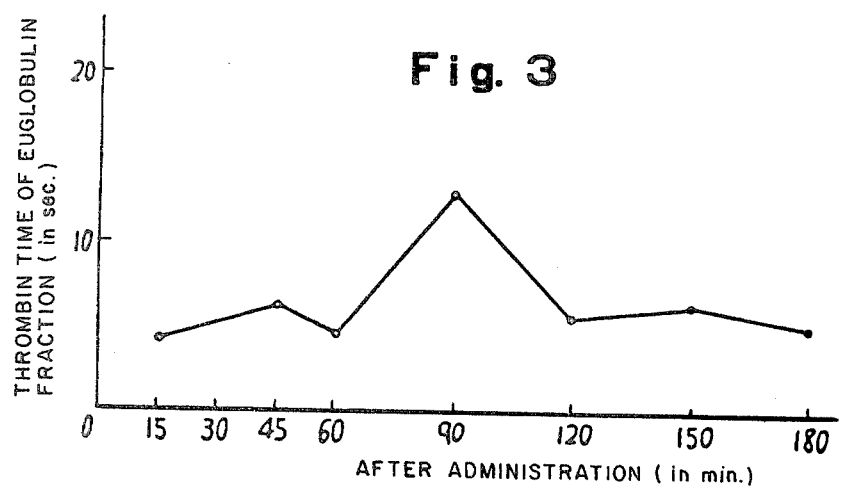

UROKINASE PREPARATION FOR ORAL ADMINISTRATION

DETAILED DESCRIPTION OF THE INVENTION

The present invention relates to a novel urokinase preparation, more particularly, a stable urokinase preparation for oral administration.

Urokinase is an enzyme extracted from human urine and has a function of converting plasminogen in blood to plasmin capable of enzymically decomposing fibrin. Accordingly, urokinase is effective for remedy of thrombosis such as cerebral thrombosis and cardiac infarction. It is known that when urokinase is used in combination with a carcinostatic agent, it exerts an effect of promoting the activity of the carcinostatic agent.

A conventional urokinase preparation is formed by freeze-drying, and at the time of administration, it is dissolved in a physiological salt solution or glucose injection solution and is administered by intravenous injection or instillation.

Ways of administering medicines for remedy of diseases are roughly classified into injection, oral administration and external application. From the viewpoint of elimination of pains to patients and troubles to doctors, it is obvious that oral administration is most preferred if an effect comparable or superior to the effect attainable by injection can be expected by oral administration.

Especially in the case of urokinase, oral administration is significant because side effects such as fever by pyrogen are readily caused by intravenous injection or urokinase as is well-known in the art.

We, the inventors found that when urokinase was applied to the intestinal tract of rabbits, as shown in Experiments 1 and 2 given hereinafter, the activity of plasmin in blood was increased. Accordingly, we considered that increase of the activity of plasmin could be expected also by oral administration of urokinase, and researches were made on oral administration of urokinase. As a result, it was found that there was a possibility of oral administration of urokinase.

However, since urokinase is ordinarily very unstable and is readily deactivated and since it is anticipated that urokinase will readily be decomposed by enzyme present in the intestines, such as trypsin and chymotrypsin, it is necessary to stabilize urokinase, in order to enable oral administration of urokinase.

Therefore, we made researches on stabilization of urokinase. As a result, it was found that when an enzyme inhibitor is incorporated into urokinase, a stable urokinase preparation suitable for oral administration is obtained. More specifically, we noted that though purified urokinase is unstable, urokinase in urine or crude urokinase is relatively stable, and we expected that a substance contributive to stabilization of urokinase would be present in urine or crude urokinase. We furthered reserches and found that certain enzyme inhibitors contained in urine in relatively large amounts, such as mingin, minginin, a high molecular substance called urine trypsin inhibitor (UTI) and analogues thereof are effective for stabilization of urokinase. Based on this finding, we developed researches. As a result, it was found that in addition to the above-mentioned enzyme inhibitors from urine, enzyme inhibitors from plants such as soybean trypsin inhibitor (SBTI) and analogues thereof, enzyme inhibitors from animal organs such as "iniprol" (Choay, France), aprotinin, a basic polypeptide consisting of 58 amino acid residues which is known under the tradename "TRASYLOL®" (Bayer A.G., West Germany) and analogues thereof, and chemically synthesized enzyme inhibitors such as $\epsilon$-aminocaproic acid, tranexamic acid, $\epsilon$-guanidinocaproic acid, p-amidinobenzoic acid and p-guanidinobenzoic acid types and analogues thereof are similarly effective for stabilization of urokinase. Further, it was found that these enzyme inhibitors inhibit actions of trypsin and chymotrypsin and consequently are effective for prevention of deactivation of urokinase in the intestines, and that the degree of stabilization of urokinase differs depending upon the mixing ratio of such enzyme inhibitor to urokinase and a better stabilizing effect can be attained when the mixing ratio is in a certain range. We have now completed the present invention based on these findings.

A primary object of the present invention is to provide a urokinase preparation suitable for oral administration which is effective for remedy of thrombosis and is comparable or superior in the curative effect to conventional urokinase preparations which are administered only by injection. In accordance with the present invention, this object can be attained by a urokinase preparation for oral administration which comprises urokinase and, incorporated therein, an enzyme inhibitor.

The present invention will now be described in detail.

It is known that urokinase includes various types differing in the molecular weight, and it has been reported that there are present types having a molecular weight of 33,000, a molecular weight of 54,000 and a molecular weight higher than 100,000, respectively. Any type of urokinase can be used in the present invention, so far as it has a relative activity of 200 to 15,000 units per mg of protein. A freeze-dried product of urokinase for injection may be used in the present invention, and such freeze-dried product may contain minor amounts of harmless impurities.

A highest stabilizing effect can be obtained when the enzyme inhibitor is incorporated in an amount of 100 to 200 units per 50 units of urokinase.

In case of oral administration, when urokinase is administered in an amount 2 to 5 times the amount administered in case of intravenous injection, a substantially identical degree of the plasmin activity can be obtained though the pattern of manifestation of the effect is different from that in case of intravenous injection.

The urokinase preparation for oral administration according to the present invention is prepared by mixing urokinase with an enzyme inhibitor (together with appropriate additives) and filling the mixture in capsules or molding the mixture into tablets. In order to prevent decomposition or deactivation of urokinase by gastric juice, enteric coating may be formed on such capsules or tablets.

In the present invention, as is apparent from the foregoing illustration, by incorporating an enzyme inhibitor into urokinase, the stability of urokinase is remarkably increased and a urokinase preparation suitable for oral administration can be obtained. More specifically, when the preparation of the present invention is orally administered, urokinase is effectively stabilized by the enzyme inhibitor, and the pharmacolgical effects (curative effect for thrombosis and effect of promoting the activity of a carcinostatic agent) possessed by urokinase can be exerted sufficiently. Thus, various advantages can be attained by the present invention.

The present invention will now be described by reference to the following Examples.

EXAMPLE 1

50 units of urokinase is mixed with 50 units of UTI (urine trypsin inhibitor) extracted from fresh human urine, and appropriate amounts of lactose and crystalline cellulose are incorporated into the mixture. Then, the resulting mixture is filled in gelatin capsules and enteric coating is formed on these capsules.

EXAMPLE 2

50 units of urokinase is mixed with 100 units of UTI (urine trypsin inhibitor) extracted from fresh human urine, and appropriate amounts of mannitol, starch and magnesium stearate are incorporated into the mixture. The resulting mixture is molded into tablets and enteric coating is formed on the tablets.

EXAMPLE 3

50 units of urokinase is mixed with 200 units of soybean trypsin inhibitor (SBTI) extracted from soybeans, and appropriate amounts of mannitol and synthetic aluminum silicate are incorporated into the mixture. Then, the resulting mixture is filled in gelatin capsules and enteric coating is formed on the capsules.

EXAMPLE 4

50 units of urokinase is mixed with 1 unit of "trasylol", which is a trypsin inhibitor extracted from a bovine organ, and appropriate amounts of mannitol, starch and magnesium stearate are incorporated into the mixture. Then, the resulting mixture is molded into tablets, and enteric coating is formed on the tablets.

EXAMPLE 5

25 units of urokinase is mixed with 25 $\mu$g of tranexamic acid, and appropriate amounts of mannitol, starch and magnesium stearate are incorporated into the mixture. Then the resulting mixture is molded into tablets, and enteric coating is formed on the tablets.

Experiments conducted so as to prove the effects of the present invention will now be described by reference to the accompanying drawings, in which:

FIG. 1 is a graph showing results of an absorption test where urokinase was administered to the rectum of a rabbit;

FIGS. 2 and 3 are graphs showing results of absorption tests were urokinase alone was orally administered.

EXPERIMENT 1

Figure 4:
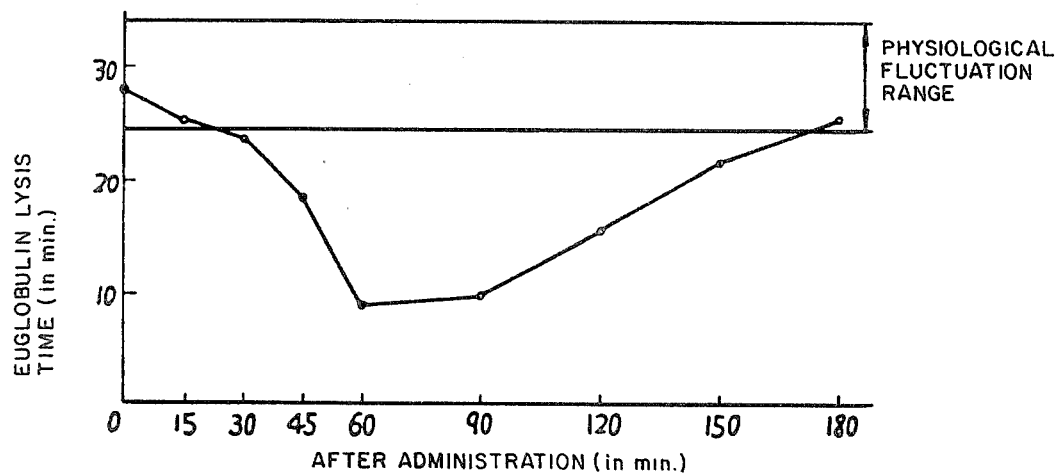
FIGS. 4 and 5 are graphs showing results of absorption tests where a mixture of urokinase and an enzyme inhibitor was orally administered.

In this Experiment, the possibility of absorption of urokinase in the rectum was examined.

A physiological salt solution containing 90,000 units of urokinase was directly administered to the rectum of a male rabbit having a body weight of 4 kg, and blood was sampled at predetermined intervals. The increase of the plasmin activity in blood was determined according to the euglobulin dissolution time method to obtain results shown in FIG. 1.

From FIG. 1, it is seen that when 30 minutes had passed from the administration, the dissolution time was shortened and the plasmin activity was increased. Thus, it has been confirmed that urokinase can be absorbed through the rectum.

EXPERIMENT 2

In this Experiment, absorption of urokinase in case of oral administration of urokinase alone was examined.

30,000 units of urokinase was solely administered orally to a healthy crossbred dog having a body weight of 4 kg and the euglobulin dissolution time and the thrombin time of euglobulin fraction were measured at predetermined intervals to obtain results shown in FIGS. 2 and 3.

As is seen from FIGS. 2 and 3, when 90 minutes had passed from the administration, the euglobulin dissolution time was shortened and the thrombin time was prolonged. Thus, absorption of urokinase was confirmed. When 120 minutes had passed from the administration, both the euglobulin dissolution time and the thrombin time were returned to normal levels.

EXPERIMENT 3

In this Experiment, the stability of urokinase was tested.

The stability test was conducted on urokinase preparations formed in Examples 1, 2 and 3 and urokinase preparations formed in the same manner as in these Examples except that the mixing ratio between urokinase and the enzyme inhibitor (UTI or SBTI) was changed. The test method was as follows.

A sample was dissolved in a tris-lysine-glycerin buffer solution having a pH of 7.4, and the solution was filtered and allowed to stand still at 37° C. for 1 to 5 hours. The change of the activity of urokinase with the lapse of time was determined according to Hestrin's method using AGLMe as a substrate.

Obtained results are shown in Tables 1 and 2. It has been confirmed that when an enzyme inhibitor is incorporated into urokinase, the stability of urokinase is increased over the stability of urokinase alone. Further, it has been confirmed that when the mixing ratio of the enzyme inhibitor to urokinase is less than 1, the stability is reduced as this mixing ratio is lowered, and that when this mixing ratio is larger than 4, the stability is not increased proportionally to the increase of the mixing ratio of the enzyme inhibitor. Accordingly, it has been found that an optimum mixing ratio of the enzyme inhibitor to urokinase is in the range of from 2 to 4 (in this range, a most preferred stabilizing effect can be obtained).

TABLE 1

| | Urokinase Activity Residual Ratio (%) | | | | | |
|---|---|---|---|---|---|---|
| | time (hour) | | | | | |
| sample | 0 | 1 | 2 | 3 | 4 | 5 |
| urokinase 50 units | 100 | 92 | 80 | 60 | 37 | 19 |
| urokinase 50 units UTI 5 units | 100 | 94 | 88 | 63 | 51 | 37 |
| urokinase 50 units UTI 10 units | 100 | 93 | 89 | 84 | 78 | 71 |
| urokinase 50 units UTI 25 units | 100 | 97 | 92 | 90 | 87 | 90 |
| urokinase 50 units UTI 50 units | 100 | 106 | 99 | 93 | 94 | 94 |
| urokinase 50 units UTI 100 units | 100 | 102 | 100 | 99 | 104 | 101 |
| urokinase 50 units UTI 150 units | 100 | 101 | 98 | 100 | 101 | 99 |
| urokinase 50 units UTI 200 units | 100 | 105 | 97 | 95 | 98 | 96 |
| urokinase 50 units | 100 | 100 | 99 | 97 | 95 | 95 |

TABLE 1-continued

| | Urokinase Activity Residual Ratio (%) | | | | | |
|---|---|---|---|---|---|---|
| | time (hour) | | | | | |
| sample | 0 | 1 | 2 | 3 | 4 | 5 |
| UTI 250 units | | | | | | |

TABLE 2

| | Urokinase Activity Residual Ratio (%) | | | | | |
|---|---|---|---|---|---|---|
| | time (hour) | | | | | |
| sample | 0 | 1 | 2 | 3 | 4 | 5 |
| urokinase 50 units | 100 | 92 | 80 | 60 | 37 | 19 |
| urokinase 50 units SBTI 5 units | 100 | 90 | 83 | 66 | 43 | 26 |
| urokinase 50 units SBTI 10 units | 100 | 91 | 86 | 80 | 72 | 63 |
| urokinase 50 units SBTI 25 units | 100 | 97 | 94 | 91 | 87 | 79 |
| urokinase 50 units SBTI 50 units | 100 | 95 | 92 | 87 | 91 | 90 |
| urokinase 50 units SBTI 100 units | 100 | 103 | 96 | 97 | 97 | 97 |
| urokinase 50 units SBTI 200 units | 100 | 101 | 100 | 99 | 98 | 99 |
| urokinase 50 units SBTI 500 units | 100 | 100 | 92 | 97 | 97 | 98 |

EXPERIMENT 4

Also in this Experiment, the stability of urokinase was tested.

The stability test was conducted on the urokinase preparation formed in Example 4 and urokinase preparations formed in the same manner except that the mixing ratio of "trasylol" to urokinase was changed, according to Hestrin's test method described in Experiment 3. Obtained results are shown in Table 3. From these results, it has been confirmed that when "trasylol" is incorporated into urokinase, the stability of urokinase is increased over the stability of urokinase alone. Further, it has been found that when the mixing ratio of "trasylol" to urokinase is less than 1/500, the stability is decreased as this mixing ratio is lowered, and that when this mixing ratio is larger than 1/50, the stabilizing effect is not increased proportionally to the mixing ratio of "trasylol". Thus, it has been confirmed that an optimum mixing ratio of "trasylol" to urokinase is in the range of from 1/100 to 1/50 (in this range, a most preferred stabilizing effect can be obtained).

TABLE 3

| | Urokinase Activity Residual Ratio (%) | | | | | |
|---|---|---|---|---|---|---|
| | time (hour) | | | | | |
| sample | 0 | 1 | 2 | 3 | 4 | 5 |
| urokinase 50 units | 100 | 90 | 82 | 63 | 34 | 21 |
| urokinase 50 units "trasylol" 0.01 unit | 100 | 91 | 82 | 75 | 61 | 55 |
| urokinase 50 units "trasylol" 0.05 unit | 100 | 93 | 90 | 81 | 74 | 68 |
| urokinase 50 units "trasylol" 0.1 unit | 100 | 92 | 91 | 86 | 81 | 76 |
| urokinase 50 units "trasylol" 0.5 unit | 100 | 100 | 97 | 95 | 88 | 85 |
| urokinase 50 units "trasylol" 1 unit | 100 | 101 | 98 | 94 | 90 | 84 |
| urokinase 50 units "trasylol" 1.5 units | 100 | 102 | 99 | 96 | 87 | 86 |
| urokinase 50 units "trasylol" 2 units | 100 | 100 | 97 | 95 | 89 | 85 |

EXPERIMENT 5

Also in this Experiment, the stability of urokinase was tested.

The stability test was conducted on the urokinase preparation formed in Example 5 and urokinase preparations formed in the same manner except that the mixing ratio of tranexamic acid to urokinase was changed. The test method was as follows.

A sample was dissolved in a 0.1 M of borate buffer solution having a pH of 8.0, and the solution was filtered and allowed to stand still at 37° C. for 1 to 5 hours. The change of the activity of urokinase with the lapse of time was determined according to Hestrin's method using AGLMe as substrate.

Obtained results are shown in Table 4. From these results, it has been confirmed that when tranexamic acid is incorporated into urokinase, the stability of urokinase is increased over the stability of urokinase alone. Further, it has been confirmed that when tranexamic acid is incorporated in an amount of 2.5 to 250 μg per 25 units of urokinase, a relatively good stability is obtained.

TABLE 4

| | Urokinase Activity Residual Ratio (%) | | | | | |
|---|---|---|---|---|---|---|
| | time (hour) | | | | | |
| sample | 0 | 1 | 2 | 3 | 4 | 5 |
| urokinase 25 units | 100 | 82 | 78 | 65 | 40 | 20 |
| urokinase 25 units tranexamic acid 0.25 μg | 100 | 90 | 80 | 65 | 45 | 30 |
| urokinase 25 units tranexamic acid 2.5 μg | 100 | 95 | 82 | 78 | 72 | 68 |
| urokinase 25 units tranexamic acid 25 μg | 100 | 78 | 70 | 70 | 63 | 55 |
| urokinase 25 units tranexamic acid 250 μg | 100 | 75 | 70 | 65 | 60 | 50 |
| urokinase 25 units tranexamic acid 1 mg | 100 | 68 | 60 | 50 | 30 | 10 |

EXPERIMENT 6

In this Experiment, the absorption test of a preparation comprising urokinase and, incorporated therein, an enzyme inhibitor was carried out.

Figure 5:
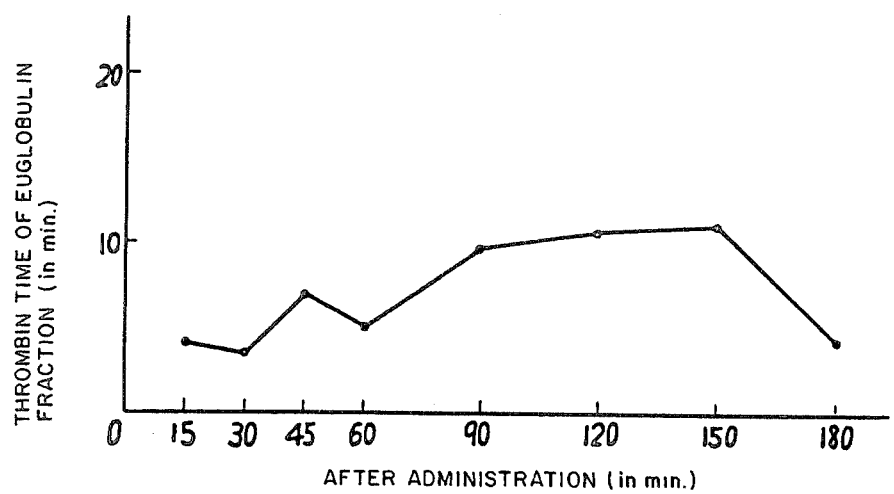

A preparation comprising 30,000 units of urokinase and 60,000 units of a trypsin inhibitor extracted from soybeans was orally administered in the form of an enteric-coated capsule to a healthy crossbred dog having a body weight of 4 kg, and the euglobulin dissolution time and the thrombin time of euglobulin fraction were determined at pedetermined intervals to obtain results shown in FIGS. 4 and 5.

From these results, it is seen that the euglobulin dissolution time was shortened when about 45 minutes had passed from the administration, the peak was maintained during a period of 60 to 90 minutes from the administration and the shortening of the euglobulin dissolution time was observed up to the point when 120 minutes had passed from the administration. Further, the thrombin time was prolonged when 60 minutes had passed from the administration and the peak was continued during a period of 90 to 150 minutes from the administration. Thus, it has been confirmed that the plasmin level in blood can be significantly increased by the urokinase preparation of the present invention. When these results are compared with the results of FIGS. 2 and 3 obtained by sole administration of urokinase, it is seen that increase of the plasmin level in blood, continuation of this increase and increase of the absorption efficiency can be attained by the preparation of the present invention comprising urokinase and, incorporated therein, an enzyme inhibitor over the case of sole administration of urokinase.

From results of the foregoing Experiments, it has been confirmed that when an enzyme inhibitor is incorporated in urokinase, the stability of urokinase and the absorption efficiency of urokinase at oral administration can be increased as compared with the case where urokinase alone is used.

What is claimed is:

1. A pharmaceutical composition with antithrombotic action for oral administration comprising an effective amount of urokinase and an effective urokinase stabilizing amount of an enzyme inhibitor which is a trypsin inhibitor extractable from human urine selected from the group consisting of mingin, minginin and urine trypsin inhibitor, together with a pharmaceutical carrier.

2. A pharmaceutical composition with antithrombotic action for oral administration comprising an effective amount of urokinase and an effective urokinase stabilizing amount of an enzyme inhibitor which is soybean trypsin inhibitor, together with a pharmaceutical carrier.

3. A pharmaceutical composition with antithrombotic action for oral administration comprising an effective amount of urokinase and an effective urokinase stabilizing amount of an enzyme inhibitor which is aprotinin, together with a pharmaceutical carrier.

4. A pharmaceutical composition with antithrombotic action for oral administration comprising an effective amount of urokinase and an effective urokinase stabilizing amount of an enzyme inhibitor which is selected from the group consisting of $\epsilon$-aminocaproic acid, tranexamic acid, $\epsilon$-guanidinocaproic acid, p-amidinobenzoic acid and p-guanidinobenzoic acid, together with a pharmaceutical carrier.

5. The pharmaceutical composition as defined in claims 1 or 2 which comprises a ratio of enzyme inhibitor units to urokinase units of from about 1 to about 4.

6. The pharmaceutical composition as defined in claim 3 which comprises a ratio of aprotinin units per urokinase units of from about 1:500 to 1:50.

7. The pharmaceutical composition as defined in claim 6 wherein the ratio is from about 1:100 to about 1:50.

8. The pharmaceutical composition as defined in claim 4 which comprises an amount of from 2.5 to 250 $\mu$g of tranexamic acid per 25 units of urokinase.

9. The pharmaceutical composition as defined in claim 5 which comprises an amount of from about 100 to about 200 units of enzyme inhibitor per 50 units of urokinase.

10. The pharmaceutical composition as defined in claim 1, 2, 3 or 4 which is in the form of capsules or tablets.

11. The pharmaceutical composition as defined in claim 10 which is in the form of capsules or tablets coated wuth an enteric coating.

* * * * *